United States Patent [19]

Hoffman

[11] Patent Number: 4,573,454
[45] Date of Patent: Mar. 4, 1986

[54] SPINAL FIXATION APPARATUS

[76] Inventor: Gregory A. Hoffman, 4167 Woodstock Dr., Fort Wayne, Ind. 46815

[21] Appl. No.: 611,475

[22] Filed: May 17, 1984

[51] Int. Cl.⁴ .............................................. A61F 5/01
[52] U.S. Cl. .................................... 128/69; 128/92 R
[58] Field of Search .................... 128/69, 92 R, 92 B, 128/92 BC, 92 E

[56] References Cited

U.S. PATENT DOCUMENTS

| | | | |
|---|---|---|---|
| 3,693,616 | 9/1972 | Roaf et al. | 128/69 |
| 3,865,105 | 2/1975 | Lode | 128/69 |
| 4,003,376 | 1/1977 | McKay et al. | 128/69 |
| 4,078,559 | 3/1978 | Nissinen | 128/69 |
| 4,269,178 | 5/1981 | Keene | 128/69 |
| 4,369,769 | 1/1983 | Edwards | 128/69 |
| 4,369,770 | 1/1983 | Bacal et al. | 128/69 |
| 4,382,438 | 5/1983 | Jacobs | 128/69 |

FOREIGN PATENT DOCUMENTS 441932 12/1974 U.S.S.R. ............................ 128/69

Primary Examiner—Richard J. Apley
Assistant Examiner—Alan W. Cannon
Attorney, Agent, or Firm—Jeffers, Irish & Hoffman

[57] ABSTRACT

A surgical implant for fixation of the human spinal column in the treatment of scoliosis, particular in very young children. The device comprises a pair of elongate bars which are rigidly connected together to form a generally rectangular appliance, and wherein the lower portion of the device is slidably connected to the upper portion so that the device is capable of extension and contraction in the longitudinal direction. In the particular embodiment disclosed, the lower fixation element is formed as a pair of sleeves connected together by a cross member with the free end portions of the bars slidably received within the sleeves thereby permitting the aforementioned longitudinal extension. The device is implanted on the posterior side of the spinal column with the bars and sleeves wired to individual vertebrae to thereby stabilize the spinal column and prevent it from reassuming the prior scoliotic curve. The fact the the device is extensible in the longitudinal direction permits the device to extend with the growth of the spine thereby preventing trunk shortening, which is a problem with other appliances used for treatment of scoliosis.

13 Claims, 7 Drawing Figures

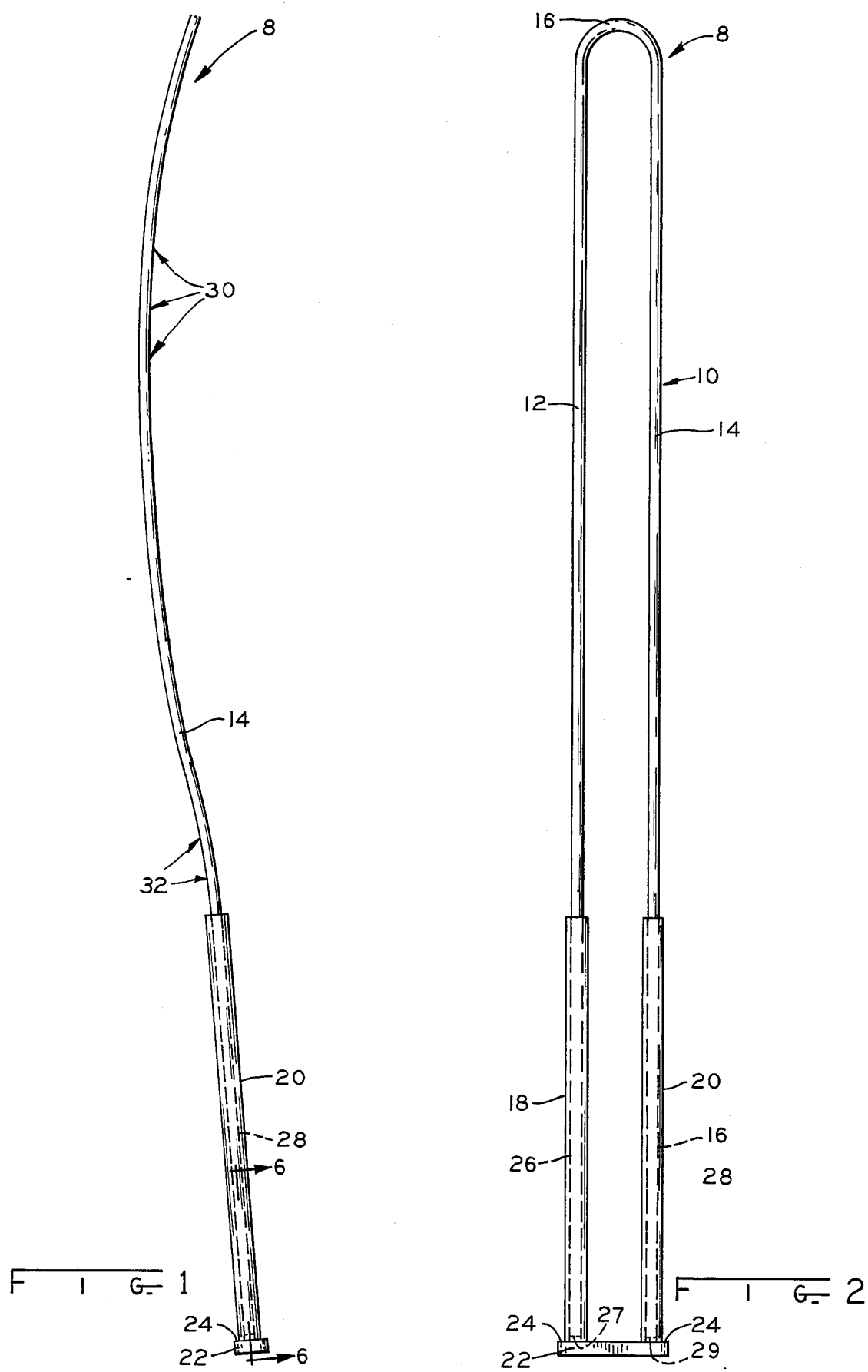

SPINAL FIXATION APPARATUS

BACKGROUND OF THE INVENTION

The present invention relates to a spinal column fixation device, and in particular to a device of this type used in the treatment of scoliosis. Scoliosis is a three dimensional curvature of the spine in which the spine, when viewed from the posterior aspect, has an abnormal lateral curvature. In additional to the lateral curvature, there is a curvature in a plane perpendicular to the axis of the spine, so that the combined curvature is somewhat spiral in nature. Scoliosis is much more prevalent in young children and adolescents than in adults, and preferentially afflicts females.

For scoliosis in an adolescent, the normal procedure of choice is the insertion of spinal instrumentation to correct the curvature immediately followed by a fusion of the spine. After the curvature has been corrected by manipulation of the metal instrumentation, the facet joints on either side of the spine in the area that is affected by the curvature are then removed and small strips of bone taken from the illiac crest area of the pelvis, for example, are laid along the posterior elements out to the tips of the transverse processes. The metal instrumentation remains attached to the spinal column to stabilize the spinal column thereby permitting the inserted strips of bone to fuse into a solid mass with the spinal column. Normally the metal instrumentation is never removed, but after the definitive fusion has taken place, the instrumentation is somewhat superfluous.

The most common type of instrumentation utilized for this procedure is the Harrington distraction and compression system wherein separate hooks, one above and one below the fusion mass, are hooked around the laminae and are connected together by a solid rod having ratchets on the upper end thereof. By manipulation of the ratchet mechanism, the hooks are spread apart, thereby pulling the curvature out of the spinal column. If compression is also utilized, lateral hooks engage the transverse processes on the convex side of the curvature and are then pulled toward the distraction rod to assist in straightening the spinal column.

A disadvantage to the Harrington system is that it is not inherently a strong system for continued fixation of the spinal column. Since there are only two points of fixation for the exertion of distraction forces, if one of the hooks fails or the rod breaks, which sometimes occurs in the areas of the ratchets, the spinal column is totally destabilized and will assume its previous scoliotic curvature if the spinal fusion has not yet completely formed. Even simple day to day activities place a tremendous amount of stress on the spinal column, and it is not unusual for metal instrumentation, such as that used in the Harrington system, to fail.

Subsequently, the Luque fixation system was developed. This system comprises two L-shaped solid rods which are wired together in the form of a rectangle with the upper cross member extending across the posterior side of the spinal column above the area of the abnormal curvature, and the lower cross member for the other, inverted rod, passing across the spinal column at a point below the curvature. This rectangular-shaped appliance is positioned against the posterior side of the spine such that the elongate rods are located on each side of the spinous processes, lying between the spinous and respective transverse processes. The rods are fixed to the spinal column by means of individual wires which are passed around the rods and underneath the posterior lamina.

The advantage of the Luque system is that it is a much stronger system than the Harrington system, primarily because of the fact that it is fixed at each segment of the spine, so that if one or two wires were to break, total fixation of the spine would not be lost. A further advantage to the Luque system is that it is strong in the direction of forces within the plane of the rectangle defined by the two L-shaped rods.

One of the disadvantages of the double L-rod Luque system is that the two elements making up the rectangle are not rigidly fixed at the corners of attachment. Accordingly, some strength against torsional forces is lost. Many of the activities that a person is involved in require twisting of the spine, so that if two much twisting is permitted, acceptable fusion of the spine may be delayed or prevented altogether. Furthermore, the potential for breaking the wires is much greater if the patient engages in activities which produce a high degree of torsional movement.

A further development to the Luque system is the provision of a solid rectangle, which results in much better stability against torsional forces.

A further development of the Luque system has resulted in a solid rectangular appliance. Although this appliance provides much better stability from the standpoint of torsional forces, the appliance must be manufactured to fit exactly the size of spine to which it will be fitted. Because there is substantial variation in the length of the human spine, it is often necessary to stock a large number of these appliances. Also, it may not be until the patient has been opened for implanting of the appliance that it is discovered the appliance on hand will not fit.

A small child, such as one below the age of 9 or 10, that has severe scoliosis presents a particularly troublesome problem that is not present in an older child or adolescent. Particularly if the child has scoliosis which is progressive, external type braces will often not be sufficient to arrest progression of the condition, and a surgical procedure is necessary.

Both the Harrington and Luque systems have been utilized in fixation of the spines of young children, but if the fusion is done at the time of initial fixation, the spine cannot grow any further and since the rest of the body will grow somewhat normally, the child ends up with an abnormally and unproportionally short trunk. From a cosmetic standpoint, this is extremely undesirable, although it is often necessary with rapidly progressing scoliosis.

If the spine is not fused at the time of initial instrumentation with the Harrington rods, the growth of the spine will progressively loosen and reduce the effectiveness of the distraction rod, so that by the time the child is ready for the definitive fusion procedure, the spine will have regained some of its original scoliotic curve, or will require repeated tightening of the Harrington rod.

Although the original double-L Luque system on a small child to fix the spine until the spine has developed to the point where the fusion procedure can be done results in stronger fixation of the spine than does the Harrington system, the two L-shaped rods tend to be pulled apart by growth of the spine, because the bars must be wired on the vertebrae sufficiently loose to enable movement of the individual vertebrae relative to each other. It has been observed that, after the passage of three or four years, the wires which previously attached the individual vertebrae to the rods are likely to have slipped off the ends of the rods. When this occurs, there is no longer any fixation of the spine and it is then able to reassume its previous scoliotic curve.

In the case of the solid rectangular Luque system, or where the double-L rod Luque system has the rods very tightly wired together so that relative sliding between the two rods is not possible, the child's spinal column will not be able to grow because it is fixed against movement in the longitudinal direction. This will result in a shortened spine and trunk just as would occur if the spine were fused at the time the instrumentation was implanted; or the wires will break under the strong forces of growth.

SUMMARY OF THE INVENTION

The disadvantages of prior spinal fixation devices used in the correction of scoliosis in small children are avoided by the spinal fixation device of the present invention, in one form thereof. The spinal fixation device according to one form of the present invention comprises a pair of generally U-shaped fixation elements which are slidably connected together so that the device is capable of extension and contraction in the longitudinal direction. By "longitudinal direction" is meant the general direction of growth of the spine. The fixation elements comprise elongate rods and sleeves which are wired to the individual laminae of the spinal column in the portion thereof where corrective forces must be applied to prevent reoccurrence of the scoliotic curve. When implanted, the bars and sleeves lie between the spinous processes and the respective transverse processes.

Since the implanted fixation device is capable of extension in the longitudinal direction, as the spine of the young child grows, the appliance extends with it. A further advantage is that the appliance functions as a closed rectangular system, which means that there are no free pivot joints about which the appliance can be twisted under torsional forces, as is the case in both the Harrington and double-L Luque system. This stabilizes the back against torsional forces, which is advantageous when the definitive fusion procedure is accomplished at some time as the child's spine has surpassed its period of rapid growth.

To enable growth of the spinal column, the wires which affix the bars to the laminae are wired sufficiently firm such that the male rods can slide in the female sleeves as the space between adjacent vertebrae increases because of growth. Additionally, enough of the free ends of the rods are received within the sleeves that the two U-shaped fixation elements will remain connected together throughout the expected growth range of the spine prior to fusion of the spine.

The invention, in accordance with one form thereof, is an implantable device for fixing the spinal column comprising a generally U-shaped first fixation element having two rigid, spaced apart and generally parallel elongate legs rigidly connected together and each having a free end portion. The legs are adapted to be located at each side of the spinous processes between the spinous and respective transverse processes. A generally U-shaped second fixation element comprising two rigid, generally parallel and spaced apart legs which are rigidly connected together are slidably connected to the free end portions of the respective legs of the first fixation element to enable longitudinal extension movement of the device to accommodate growth of the spinal column.

In a preferred form of the invention, the second fixation device comprises a pair of sleeves within which the free end portions of the rods and the terminal ends of the rod of the first fixation element are slidably received. This is advantageous in that the sleeves, which are generally cylindrical in shape, can be wired directly to the lower one of the two vertebrae in a fashion similar to the bars of the upper fixation element. Although the use of sleeves for the sliding connection between the upper and lower fixation elements is preferred, other types of sliding mechanical interconnections, such as dovetail and pin and slot connections, may be used.

In accordance with another form of the invention, there is provided a spinal column implant comprising an elongate extensible fixation device comprising a first generally U-shaped fixation element having two rigid, spaced apart bars rigidly connected together at one end of the first fixation device, wherein each bar has a free end portion opposite the one end of the fixation element, and a second generally U-shaped fixation element comprising two generally parallel spaced apart legs that are connected together. The first fixation element free ends are slidably connected to the second fixation element to permit longitudinal extension of the fixation device. The bars and legs lie along the spinal column at each side of the spinous processes between the spinous and respective transverse processes. The bars and legs are tied to a plurality of vertebrae in the spinal column to fix the fixation device to that portion of the spinal column including the vertebrae tied thereto. The fixation device is longitudinally extensible through the slidable connection between the first and second fixation elements to accommodate growth of the spinal column.

Since the spinal fixation device in accordance with the preferred form of the present invention is a closed rectangular system, it will more effectively resist rotational forces, thereby resulting in better correction of the rotation of a scoliotic spine in planes perpendicular to the axis of the spine.

Preferably, the second fixation element comprises a pair of ridgly connected and spaced apart sleeves within which the free ends of the first fixation element are slidably received so that the two fixation devices can be extended and contracted longitudinally thereby permitting relatively normal growth of the spine, and also enabling adjustment of the appliance to the proper length for implantation over a range of spinal column lengths.

It is an object of the present invention to provide a signal fixation device which is extensible in the longitudinal direction thereby elongating as the spine grows and avoiding the shortened trunk phenomenon that would otherwise occur if the spine is fixed against growth in younger children.

It is a further object of the present invention to provide a spinal fixation device that is particularly adapted for treating scoliosis in young children prior to full development of their spinal columns.

A still further object of the present invention is to provide a spinal fixation device that permits axial growth of the spine yet provides a strong stable system which prevents rotational deformity or progressive lateral curvature deformity until spinal fusion can be performed.

BRIEF DESCRIPTION OF THE DRAWINGS

FIG. 1 is a side elevational view of the spinal fixation device according to one form of the present invention;

FIG. 2 is a rear elevational view thereof;

DETAILED DESCRIPTION OF A PREFERRED EMBODIMENT

Figure 3:
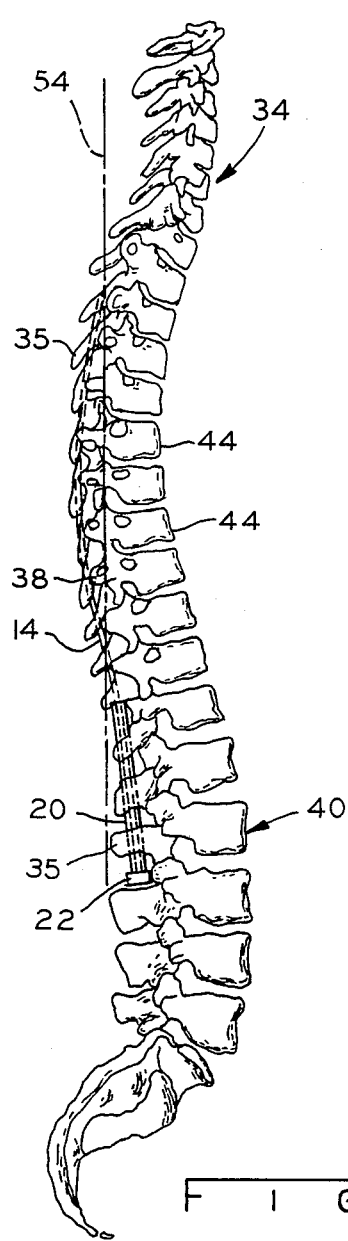
FIG. 3 is a side elevational view showing the device implanted within a human spinal column.

Referring initially to FIGS. 1 and 2, the spinal fixation device 8 comprises an upper fixation element 10 made of surgical type stainless steel and bent in a generally U-shaped configuration to comprise a pair of legs or bar elements 12 and 14 that are generally parallel and spaced apart from each other, and a cross member portion 16. Bars 12 and 14 and cross portion 16 are integral with each other. Device 8 also includes a lower fixation element 16 that is similarly U-shaped, and includes a pair of cylindrical sleeves 18 and 20 rigidly connected together by a cross member 22, that has edge portions 24 extending laterally beyond sleeves 18 and 20 for the purpose of preventing the lower fixation wires from slipping off, as will be described in greater detail below.

The lower, free end portions 26 and 28 of bars 12 and 14, respectively, are slidably received within sleeves 18 and 20 so that device 8 is extensible in the longitudinal direction in a manner similar to the slide of a trombone. The terminal ends 27 and 29 of bars 12 and 14 are completely contained inside sleeves 18 and 20. When upper fixation element 10 and lower fixation element 16 are interconnected as shown in FIGS. 1 and 2, device 8 is fairly rigid against forces in all directions except in the longitudinal direction, wherein unrestricted movement is permitted in view of the sliding connection between elements 10 and 16. Although device 8 permits a certain degree of torsional movement to accommodate some twisting of the spine, this movement is more restricted than in the case of the double-L Luque system described earlier.

The upper portion 30 of bars 12 and 14 are convex in the posterior to anterior direction to accommodate normal kyphosis of the spine, and the lower portion 32 thereof is somewhat concave in the posterior to anterior direction to accommodate normal spinal lordosis. Free end portions 26 and 28 are preferably straight, as are sleeves 18 and 20, so that easy sliding movement can be achieved, and device 8 can extend in the longitudinal direction without altering the position of upper fixation element 10 in the anterior-posterior direction.

The material for upper and lower fixation elements 10 and 16 will include those materials normally used in orthopedic implants, such as stainless steel, sudable plastics, and the like.

Figure 4:
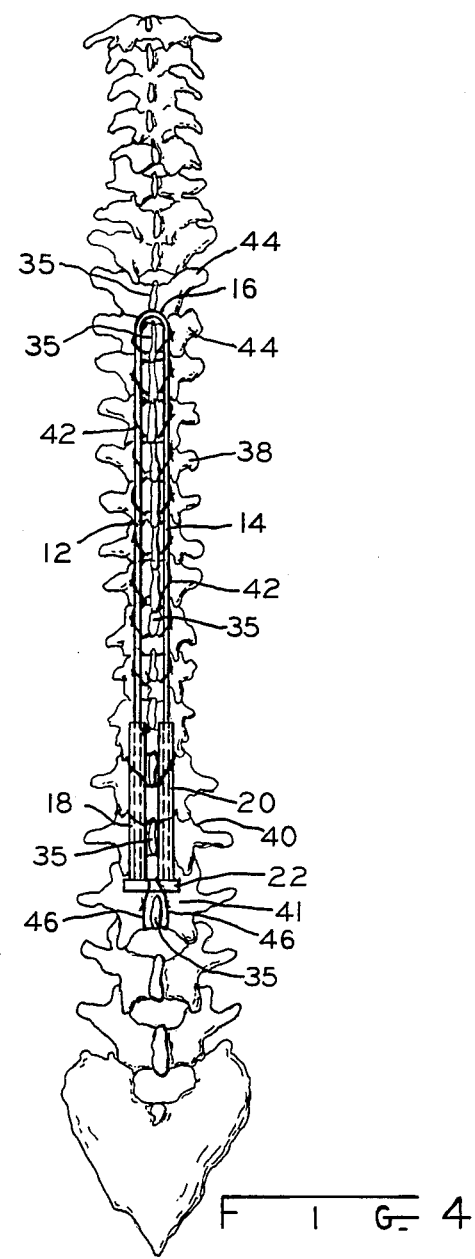
FIG. 4 is a rear elevational view showing the implanted device.
Figure 5:
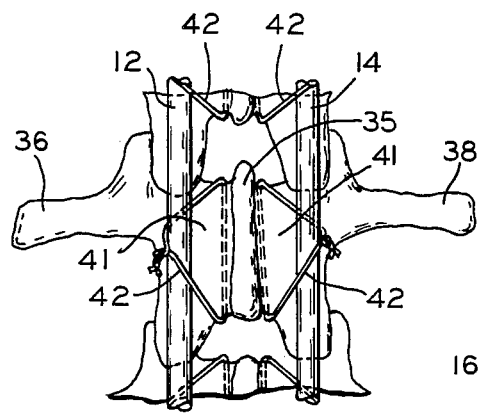
FIG. 5 is an enlarged rear elevational view illustrating the manner of fixing the device to an individual vertebra.

Referring now to FIGS. 3 through 5, the manner of implanting device 8 will be described. Fixation device 8 is sized according to the length of the child's spine and the degree and location of the scoliotic deformity. Device 8 is laid along the posterior side of the spinal column 34 such that bars 12 and 14 lie on opposite sides of the spinous processes 35 between the spinous and respective transverse processes 36 and 38 of each vertebra in the area of spine 34 to be fixed. Lower fixation element 16 is positioned such that cross member 22 is below the lowermost spinous process 35 of the area of spine 34 to be fixed, which is typically on one of the lumbar vertebrae 40, as illustrated in FIGS. 3 and 4.

The soft tissue ligamentum structure between each spinous process is removed and wires 42 are passed around the lamina 41 between the spinal cord (not shown) and lamina 41, and wires 42 are then twisted to draw bars 12 and 14 against the lamina 41. The degree of tightening should be such that spine 34 is fixed. Cross member 22 of lower fixation element 16 is typically anchored in the lumbar region by a pair of wires 46 that extend over cross member 22 on opposite sides of spinous process 35 and around the lamina 41 between the lamina and the spinal cord. Upper cross portion 16 extends between the spinous processes 35 of the adjacent vertebrae 44 at the upper extent of the region of spine 34 to be stabilized.

Figure 6:
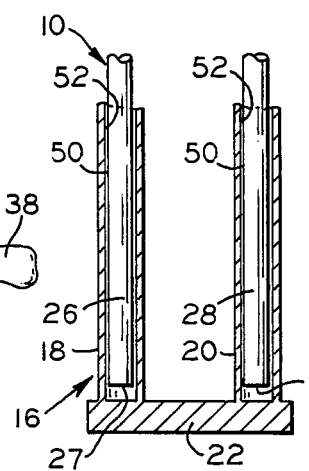
FIG. 6 is a sectional view taken along line 6—6 of FIG. 1 and viewed in the direction of the arrows.
Figure 6A:
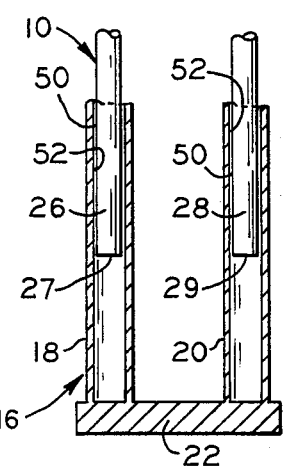
FIG. 6a is a view similar to FIG. 6 wherein the device has been extended due to axial growth of the spine.

As spine 34 grows, fixation device 8 can extend in the longitudinal direction by virtue of the sliding connection between free end portions 26 and 28 of upper fixation element 10 and sleeves 18 and 20. FIG. 6 illustrates the relative positions of upper and lower fixation elements 10 and 16 when device 8 is implanted and FIG. 6a illustrates the relative positions of elements 10 and 16 after several years of growth. It will be noted that free end portions 26 and 28 of bars 12 and 14 slide upwardly within sleeves 18 and 20 to accommodate the longitudinal extension, yet do not slide completely out of sleeves 18 and 20, thereby maintaining the rigidity of device 8. Even after the passage of a number of years, spine 34 remains stabilized until the definitive fusion procedure can be performed. The clearance between the outer surfaces 50 of free end portions 26 and 28 and the inner surfaces 52 of sleeves 18 and 20 is sufficiently close that appliance 8 remains preferably rigid against torsional forces and forces within plane 54, which is perpendicular to the posterior-anterior direction (FIG. 3), yet sufficiently loose to enable easy sliding movement between upper and lower fixation elements 10 and 16. Device 8 is a closed rectangle thereby providing good stability against such torsional forces and forces within plane 54, as opposed to the double-L Luque system wherein the connections at the corners can permit relative movement between the two halves of the Luque device.

Normally, there is a 20° to 30° kyphosis in the upper part of the spine and a 20° to 30° lumbar lardosis in the lower part of the spine. As shown in FIGS. 1 and 3, upper fixation element 10 is bent to accommodate this kyphosis and lordosis. To avoid exaggerated curvature as the spine grows, however, the bends in portions 30 and 32 are typically 10° less. For example, the convexity and concavity in portions 30 and 32 of upper fixation element 10 may be approximately 10°, depending, of course, on the configuration of the patient's spine.

While this invention has been described as having a preferred design, it will be understood that it is capable of further modification. This application is, therefore, intended to cover any variations, uses, or adaptations of the invention following the general principles thereof and including such departures from the present disclosure as come within known or customary practice in the art to which this invention pertains and fall within the limits of the appended claims.

What is claimed is:

1. An implantable device for fixing the spinal column comprising:

a generally U-shaped first fixation element comprising two rigid, spaced apart, generally parallel elongate legs rigidly connected together and each having a free end portion terminating in an end, said legs adapted to be located at each side of the spinous processes between the spinous and respective transverse processes, a generally U-shaped second fixation element comprising two rigid, generally parallel, spaced apart elongate sleeves rigidly connected together, the free end portions of the respective legs of said first fixation element being telescopically slidably received in said sleeves for longitudinal extension movement, the legs of said first element terminating within said sleeves such that the ends are completely disposed in said sleeves whereby the device is capable of lengthening in the direction of growth of the spinal column after implantation on the spine.

2. The device of claim 1 wherein: said first fixation element includes a first cross member connecting said first element legs together, said second fixation element includes a cross member connecting said sleeves together, and said cross elements are located at opposite ends of said device.

3. The device of claim 2 wherein said first and second cross elements are the only cross elements and the space bounded by said legs and cross elements is open.

4. An implantable device for fixing the spinal column comprising:

a generally U-shaped first fixation element comprising two rigid, spaced apart, generally parallel elongate legs rigidly connected together by a cross portion located at one end of the first fixation element and each leg having a free end portion opposite said cross portion, said legs adapted to be located at each side of the spinous processes between the spinous and respective transverse processes, said first fixation element adapted to extend generally in a plane including the spinal column and extending perpendicular to the posterior to anterior direction, and a second generally U-shaped fixation element comprising two generally parallel, elongate spaced apart legs rigidly connected together by a cross member at one end of the second element legs, each of said second fixation element legs being of sufficient length to extend along and be located at one side of a plurality of spinous processes between the spinous and respective transverse processes, the free end portions of said first fixation element legs being slidably connected to said second fixation element legs for relative contraction and extension of the overall length of the connected first and second element assembly in the longitudinal direction lying in said plane, but restrained against relative movement in directions within the plane transverse to the longitudinal direction.

5. The device of claim 4 wherein the legs of said first fixation element are curved convexly in an upper portion thereof and curved concavely in the lower portion thereof to generally follow the curve to the spine, and said free end portions and said second fixation element legs are substantially straight.

6. The device of claim 4 wherein: said second fixation element legs are straight sleeves, said first fixation element free end portions are slidably received in said sleeves and have terminal ends that are disposed inside said sleeves, the legs of said first fixation element are curved convexly in an upper portion thereof and curved concavely in the lower portion thereof to generally follow the curve of the spine.

7. The device of claim 4 wherein said first fixation element is a bent metal rod and said first fixation element legs and cross member are integral with each other.

8. A spinal column implant comprising: an elongate extensible fixation device comprising a first generally U-shaped fixation element having two rigid, spaced apart bars rigidly connected together at one end of the first fixation device, each bar having a free end portion opposite said one end of the fixation element, the free end portion terminating in an end, and a second generally U-shaped fixation element comprising two generally parallel, elongate, spaced apart legs connected together; said first fixation element free ends being slidably connected to said second fixation element legs to permit longitudinal extension of said fixation device, said bars and legs each lying along the spinal column at each side of a plurality of the spinous processes between the spinous and respective transverse processes; said bars and legs each being tied to a plurality of vertebrae in the spinal column to fix the fixation device to that portion of the spinal column including the vertebrae tied to the fixation device; said fixation device having an overall length dimension which is longitudinally extensible while implanted through the slidable connection between the first and second fixation elements whereby the fixation device lengthens as the spinal column grows.

9. The implant of claim 8 wherein said second fixation element legs are sleeves in which said first fixation element free end portions and ends are slidably received, the length of the free end portions within the sleeves being greater than the expected growth of the spinal column.

10. The implant of claim 8 wherein the bars are tied to the vertebrae by means of wires that extend around the laminae and said bars.

11. A spinal column implant comprising: an elongate extensible fixation device comprising a first generally U-shaped fixation element having two rigid, spaced apart bars rigidly connected together at one end of the first fixation device, each bar having a free end portion opposite said one end of the fixation element, and a second generally U-shaped fixation element comprising two generally parallel, spaced apart elongate sleeves connected together, the free end portions of said bars being slidably received in said sleeves, said free end portions including terminal ends being inside said sleeves; said bars and sleeves lying along the spinal column at each side of the spinous processes between the spinous and respective transverse processes; said bars and sleeves being tied to a plurality of vertebrae in the spinal column to fix the fixation device to that portion of the spinal column including the vertebrae tied to the fixation device; said fixation device being longitudinally extensible through the slidable connection of the rods and sleeves to accommodate growth of the spinal column.

12. The implant of claim 11 wherein the portion of the first fixation element lying along the upper portion of the spinal column is convexly curved from the posterior perspective and the portion of the first fixation element lying along the lower portion of the spinal column is concavely curved from the posterior perspective.

13. The implant of claim 12 wherein the convexity of the first fixation element is less than the normal kyphosis for the spinal column to compensate for spinal column growth.

* * * * *